United States Patent
Fan et al.

(10) Patent No.: US 9,244,169 B2
(45) Date of Patent: Jan. 26, 2016

(54) MEASURING ACOUSTIC ABSORPTION OR ATTENUATION OF ULTRASOUND

(75) Inventors: Liexiang Fan, Sammamish, WA (US); Paul Donald Freiburger, Seattle, WA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 60 days.

(21) Appl. No.: 13/532,559

(22) Filed: Jun. 25, 2012

(65) Prior Publication Data
US 2013/0345565 A1    Dec. 26, 2013

(51) Int. Cl.
| G01S 15/89 | (2006.01) |
| A61B 8/08 | (2006.01) |
| A61B 8/00 | (2006.01) |
| G01S 7/52 | (2006.01) |
| A61N 7/02 | (2006.01) |

(52) U.S. Cl.
CPC ............. G01S 15/8952 (2013.01); A61B 8/08 (2013.01); A61B 8/4477 (2013.01); A61B 8/485 (2013.01); A61B 8/5207 (2013.01); A61N 7/02 (2013.01); G01S 7/52042 (2013.01); A61B 8/461 (2013.01); G01S 7/52022 (2013.01)

(58) Field of Classification Search
CPC .......... A61B 8/00; A61B 8/08; A61B 8/4477; A61B 8/461; A61B 8/485; A61B 8/5207; A61B 5/00; A61N 7/02; G01S 15/8952; G01S 7/52042; G01S 7/52022
See application file for complete search history.

(56) References Cited

U.S. PATENT DOCUMENTS

| 4,619,267 A | 10/1986 | Lannuzel et al. |
| 6,012,779 A | 1/2000 | Morris |
| 2007/0230759 A1 | 10/2007 | Tamura |
| 2009/0005682 A1 | 1/2009 | Fan et al. |
| 2009/0056453 A1* | 3/2009 | McAleavey ............... 73/597 |
| 2010/0016718 A1 | 1/2010 | Fan et al. |
| 2010/0069751 A1* | 3/2010 | Hazard et al. ............. 600/438 |
| 2010/0249590 A1 | 9/2010 | Kanayama et al. |
| 2011/0060221 A1 | 3/2011 | Fan et al. |
| 2012/0108968 A1 | 5/2012 | Freiburger et al. |

FOREIGN PATENT DOCUMENTS

| CN | 1279054 | 1/2001 |
| CN | 1723856 | 1/2006 |
| DE | 38 12 434 | 4/1988 |

OTHER PUBLICATIONS

Hsu, Acoustic Radiation Force Impulse Imaging of Myocardial Performance, Thesis, 2009.*
Palmeri et al., Characterizing Acoustic Attenuation of Homogeneous Media Using Focused Impulsive Acoustic Radiation Force, Ultrason Imaging. Apr. 2006; 28(2): 114-128.*

(Continued)

*Primary Examiner* — Bo J Peng

(57) ABSTRACT

Acoustic absorption or attenuation of ultrasound is measured. To estimate acoustic absorption or attenuation, the displacement of tissue caused by stress at different frequencies is measured. The absorption or attenuation is calculated from the displacements. The incorporation of different frequencies provides another variable for solving for attenuation or absorption despite unknown tissue stiffness.

19 Claims, 3 Drawing Sheets

(56) References Cited

OTHER PUBLICATIONS

Kemmerer et al., A New Approach for Detecting Attenuation Changes During High-Intensity Focused Ultrasound, 2010 IEEE International Ultrasonics Symposium Proceedings.*

Mark L. Palmeri et al., "Characterizing Acoustic Attenuation of Homogeneous Media Using Focused Impulsive Acoustic Radiation Force," webpages, http://www.ncbi.nlm.nih.gov/pmc/articles/PMC1876707/, pp. 1-8, Apr. 28, 2006.

* cited by examiner

US 9,244,169 B2

MEASURING ACOUSTIC ABSORPTION OR ATTENUATION OF ULTRASOUND

BACKGROUND

The present embodiments relate to measuring attenuation of ultrasound. As acoustic energy propagates through tissue, the acoustic energy attenuates. The amount of attenuation may be indicative of properties of the tissue.

Attenuation may be measured with ultrasound. The change in echo intensity (e.g., B-mode amplitude) is measured to estimate the attenuation. However, speckle noise may affect the accuracy of estimates from echo intensity.

Acoustic radiation force may be used to measure attenuation. Displacements at different depths are determined in response to a constant lateral focal configuration. The displacements are used to estimate the attenuation. However, the displacement is also a function of tissue stiffness. Relying just on displacement at different depths may be inaccurate.

BRIEF SUMMARY

By way of introduction, the preferred embodiments described below include methods, instructions, and systems for measuring acoustic absorption or attenuation of ultrasound. To estimate acoustic absorption or attenuation, the displacement of tissue caused by stress at different frequencies is measured. The absorption or attenuation is calculated from the displacements. The incorporation of different frequencies provides another variable for solving for attenuation or absorption despite an unknown tissue stiffness.

In a first aspect, a method is provided for measuring acoustic absorption of ultrasound. A transducer transmits a first acoustic beam. Reference information representing tissue in a reference position is received in response to the transmission of the first acoustic beam. The transducer transmits a second acoustic beam at a second center frequency. A second displacement from the reference position caused by the transmission of the second acoustic beam is tracked. The transducer transmits a third acoustic beam at a third center frequency. The third center frequency is different from the second center frequency. A third displacement from the reference position caused by the transmission of the third acoustic beam is tracked. Acoustic absorption of the tissue is calculated as a function of the second and third displacements. The acoustic absorption is displayed.

In a second aspect, a non-transitory computer readable storage medium has stored therein data representing instructions executable by a programmed processor for measuring acoustic attenuation of ultrasound. The storage medium includes instructions for detecting displacements of tissue with ultrasound in response to stresses at different frequencies, and calculating acoustic attenuation as a function of the displacements responsive to the stresses at the different frequencies.

In a third aspect, a system is provided for measuring acoustic absorption of ultrasound. A beamformer is operable to generate acoustic radiation force of different frequencies at different times. A processor is configured to determine spatial offsets of tissue in response to the acoustic radiation force of different frequencies at the different times and to determine an acoustic absorption of the tissue as a function of the spatial offsets.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Absorption of acoustic energy is converted into radiation force, which induces tissue displacement. By measuring displacements generated by an acoustic radiation force impulse, the attenuation parameter may be inferred. A series of tissue displacement data is measured. Since displacement is also a function of tissue stiffness, more than one equation between displacement and the absorption parameter is used in order to estimate the absorption parameter. By changing the transmit frequency of the acoustic radiation force impulses while keeping the other acoustic parameters similar, multiple displacement and frequency pairs are obtained. The acquired tissue displacement data is the result of acoustic radiation force applied to the tissue at difference frequencies. The attenuation parameter and its relationship to frequency may be solved. The acoustic absorption or attenuation parameter is estimated from this data.

The absorption parameter may be used as diagnostic information, such as indicating tissue characteristics indicative of liver fibrosis, breast density, cartilage damage, bone density, celiac disease, or other conditions. The absorption parameter may be used to adjust settings for ultrasound imaging and/or therapy, such as adjusting settings for acoustic thermal treatment planning.

Figure 1:
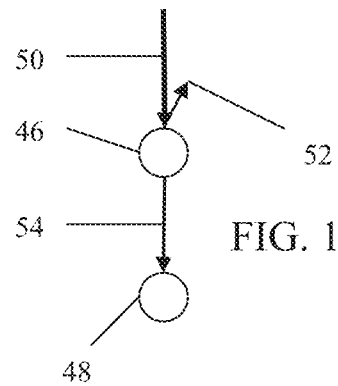
FIG. 1 illustrates, generally, acoustic attenuation and absorption.

FIG. 1 illustrates, generally, acoustic attenuation and absorption. Acoustic energy 50 propagates to a location 46. The location 46 absorbs some acoustic energy. Other acoustic energy refracts and scatters from the location 46. The arrow 52 represents refraction and scattering. The magnitude and average direction of the refraction and scattering 52 may be different from shown. In general, the refraction and scattering 52 are substantially less than absorption, such as being 10% or less of the absorption. The remaining acoustic energy propagates along line 54 to the next location 48. The difference between the incident acoustic energy 50 and the linearly propagating energy 54 is the attenuation (absorption plus refraction and scattering). Given the similarity in magnitude between attenuation and absorption, either parameter may be used. An estimation of attenuation may be an estimation of absorption or vice versa based on an assumption of a relatively small refraction and scattering. Acoustic attenuation includes absorption, refraction and scattering, but absorption is the major contributor.

FIG. 1 is a simplification. The absorption, scattering, and refraction occur for all locations through which the acoustic energy propagates. FIG. 1 represents a decretization of the propagation by having specific locations 46, 48. Other representations may be used.

Figure 2:
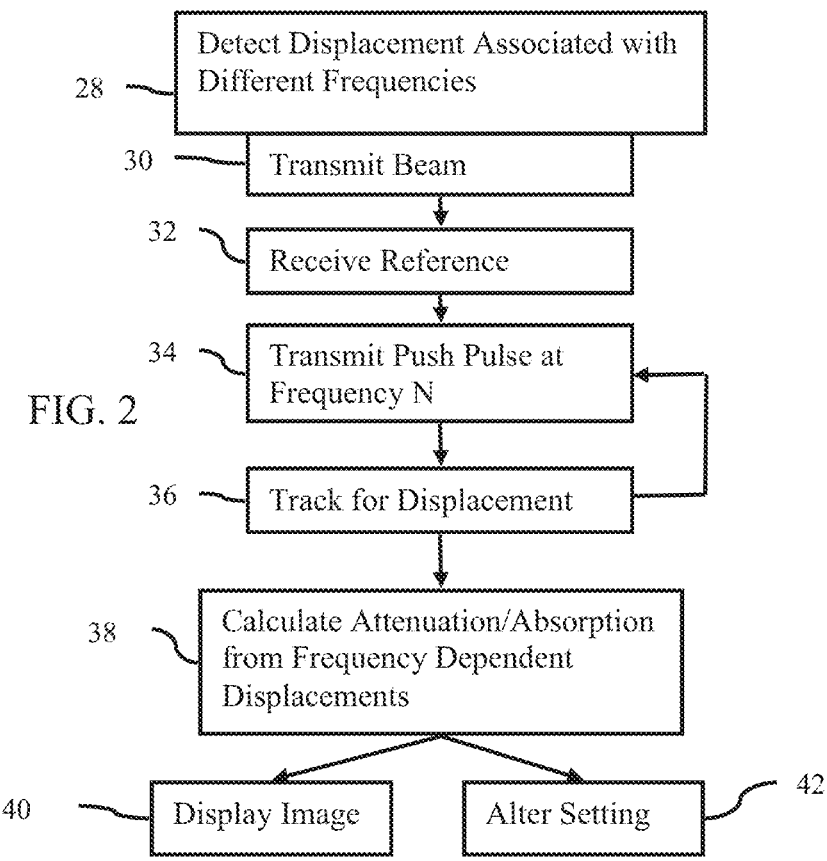
FIG. 2 is a flow chart diagram of one embodiment of a method for measuring acoustic absorption of ultrasound.

FIG. 2 is a method for measuring acoustic absorption of ultrasound. The method is implemented by the system of FIG. 5 or a different system. Additional, different, or fewer acts may be provided. For example, the detection of act 28 uses acts 30, 32, 34, and 36 or is performed without acts 30, 32, 34, and/or 36. As another example, acts 40 and/or 42 are not performed. The acts are performed in the order described or shown, but may be performed in other orders. For example, the reference information (acts 30 and 32) may be acquired after the tracking of displacement of act 36 or between acts 34 and 36.

In act 28, displacement of tissue is detected with ultrasound. Ultrasound scanning is used to measure motion of tissue. In response to an impulse stress, tissue may move. Using B-mode, Doppler (e.g., tissue motion), or other scanning, the movement along one, two, or three dimensions is detected. Any displacement measurement techniques may be used, such as associated with elasticity imaging, strain imaging, acoustic radiation force imaging (ARFI), or shear wave imaging.

In one embodiment, any induced wave imaging may be used. Acoustic energy is used to induce a wave in a region of a patient. The acoustic energy is a pushing pulse for moving the tissue. The region is scanned to track or detect the induced wave. The displacement of tissue due to the wave traveling through the region indicates the presence of the wave. The timing associated with the displacement may be used to determine velocity of the wave.

Different types of waves may be generated and/or tracked. Longitudinal waves are tracked for acoustic radiation force imaging, such as elastography or strain imaging. Shear waves are tracked for shear wave or shear wave velocity imaging.

For calculating attenuation or absorption, the impulse stress is applied at different frequencies. The pushing pulse is repeated, with each repetition being at a different frequency. The displacements caused by the pushing pulses at different frequencies are measured.

Acts 30, 32, 34, and 36 represent one embodiment of induced wave imaging, such as associated with inducing displacement by a longitudinal wave along an axial direction with acoustic radiation force. Fewer or additional acts may be provided for ARFI techniques or for other induced wave techniques. For example, signals associated with tracking in act 36 may be used for reference, allowing operation without acts 30 and 32. As another example, shear wave imaging and corresponding acts are used.

In act 30, a transducer transmits an acoustic beam. A beamformer uses relative phasing and/or delays to focus acoustic energy at a point, line, or region along a scan line. The transducer includes an array of elements that receive delayed and apodized waveforms from the beamformer. The elements convert the electrical energy to acoustic energy. The acoustic energy coherently converges as the acoustic beam along a scan line in the patient. The scan line extends from the transducer to the focal location. The scan line defines a depth or axial dimension.

The transmission of the acoustic beam is for B-mode imaging. A single pulse of about 1-5 cycles is transmitted. The waveforms are square waves associated with pulsers, but may be sinusoidal or other waveforms. The pulse is at any desired frequency, such as a center frequency of the transducer bandwidth. Multiple pulses may be used, such as associated with Doppler or contrast agent imaging.

In act 32, reference information is received. The transmission of act 30 and the responsive receipt of information in act 32 occur with the tissue being scanned at rest or not subject to externally applied impulse stress. The tissue may be subject to internal and/or transducer pressure stress, but acoustic radiation force, force from a thumper, force from manual palpitation, or other wave inducing stress is not provided. To estimate tissue displacement, echo signals before an acoustic radiation force impulse are acquired. In other embodiments, the reference information is acquired early or late relative to application of stress, such as associated with just starting to be displaced or almost relaxed after stress.

The information is received as acoustic reflection. The tissue reflects some acoustic energy from the transmitted beam. By using beamforming, Fourier analysis or other technique, the reflections from the tissue are sampled. For example, acoustic reflections impinge on the elements of the transducer. The elements convert the acoustic energy to electrical energy. Using delays and/or phasing, the electrical energy from different channels or elements is beamformed. Dynamic focusing is provided to sample along more than one location of the scan line to form a receive beam. The sampling is along the same scan line as the transmit beam, but may be at an offset location in other embodiments.

The receive processing, such as beamformation with or without detection, is for B-mode imaging. With detection, the received information represents intensities for the sample locations. The intensities representing the reflectivity of the tissue at the corresponding locations. In other embodiments, the receive processing is for Doppler or contrast agent imaging.

In act 34, another acoustic beam is transmitted from the transducer. The acoustic beam is transmitted along the same scan line, but has different characteristics than the beam transmitted in act 30. The transmission of act 34 is to generate impulse stress for displacing the tissue. The acoustic energy acts as an impulse excitation.

In an acoustic radiation force example, a 400 cycle transmit waveform with power or peak amplitude levels similar or higher than B-mode transmissions for imaging tissue is transmitted. In one embodiment, the transmission is a radiation force sequence applied to the field of view. Any acoustic radiation force imaging (ARFI) sequence may be used. Any number of cycles may be used. Any amplitude may be used. Due to the greater number of cycles in act 34 as compared to act 30, the transmit beam of act 34 has a greater power than the transmit beam of act 30. Greater power may alternatively or additionally result from a greater amplitude, aperture size, different frequency, or combinations thereof.

The transmission is configured by power, amplitude, timing or other characteristic to cause stress on tissue sufficient to displace the tissue at one or more locations. For example, a transmit focus is positioned near a bottom, center of the field of view to cause displacement throughout the field of view. The transmission may be repeated for different sub-regions. Where displacement at one location or just locations around the focal region is used, the focus is positioned at the desired region.

The acoustic energy is focused, resulting in a three-dimensional beam profile. The excitation is focused using a phased array and/or mechanical focus. The excitation may be unfocused in one dimension, such as the elevation dimension. The excitation is transmitted into tissue of a patient.

The transmitted beam has a center frequency. The electrical waveforms used to generate the beam have the center frequency. The center frequency is positioned within a bandwidth of the transducer. For example, the center frequency is between 4 and 7 MHz or between 1.8 and 3.5 MHz. The center frequency is the same or different from used in act 30.

Any center frequency may be used. The transmission to induce displacement is repeated with different center frequencies. For the different repetitions of the transmission of act 34, a different center frequency is used. For example, act 34 is performed twice. The first center frequency is at a lower end of the transducer bandwidth (e.g., 5 MHz in a 4-7 MHz bandwidth transducer) and the second center frequency is at a higher end of the transducer bandwidth (e.g., 6 MHz). Any distribution of center frequencies with one or more repetitions may be used.

For performance of act 34 at different times, other transmit conditions are maintained the same. For example, the pulse length or duration is maintained the same. The pulse length is set to 100 microseconds. In one embodiment, the duration is at least 50 microseconds. Greater or lesser duration may be used. The number of cycles may vary due to the difference in center frequency, but the duration is the same. As another example, the amplitude of the transmit beam is the same. The amplitude may be different due to regulatory limits on transmit power. Given similar or the same settings other than center frequency, the cause of any bias in displacement is based on any non-uniformity of system and transducer transmit frequency dependency. When a certain range of the spectrum of the transducer is used, the bias may be minimized or compensated based on experimentally determined adjustments and/or calibration. The remaining factor or bias may be probe variation, which is common for any detection method. The bias may be ignored in other embodiments.

In response to the transmit beam generated in act 34, a wave is generated. The tissue is forced to move in the patient. The transmitted excitation causes displacement of the tissue. At the focal point or region, a longitudinal, shear and/or other type of wave are generated in the tissue. For example, a longitudinal wave is generated and propagates from the focal region. As the wave travels through tissue, the tissue is displaced.

In act 36, displacement from the reference position caused by the transmission of the acoustic beam in act 34 is tracked. The tracking determines a single displacement. Alternatively, the tracking is performed over time to determine a sequence of displacements as the induced wave propagates. A temporal profile of displacement at a location is measured.

To track the displacement, a region of the patient is scanned with ultrasound. The displacement is detected with ultrasound scanning. A region, such as the scan line (one-dimensional), a region of interest (two or three-dimensional), entire field of view, or sub-region of interest, is scanned with ultrasound. To measure displacement at different times, the scanning is repeated.

For a given time, ultrasound is transmitted to the tissue or region of interest. Any now known or later developed displacement imaging may be used, such as transmissions for B-mode imaging. For example, pulses with 1-5 cycle durations are used with an intensity of less than 720 mW/cm². Pulses with other intensities may be used. The transmission is at any frequency, such as the same center frequency used for the transmission in act 30. The center frequency for tracking is the same or different from the center frequencies used for one, some, or all of the pushing pulses transmitted in act 34. As the center frequency for the repetitions of the pushing pulses vary, the center frequency for tracking stays the same.

The center frequency for tracking may vary as well. Other characteristics of the transmit beam of act 36 are the same as for act 30, but may be different.

Echoes or reflections from the tracking transmission are received in act 36. The echoes are beamformed, and the beamformed data represents one or more locations. To detect the displacement, ultrasound energy is transmitted to the tissue undergoing displacement and reflections of the energy are received. Any transmission and reception sequence may be used.

By performing the transmitting and receiving multiple times, data representing a one, two, or three-dimensional region at different times is received. The frequency of this repetition is the pulse repetition frequency. The transmission and reception are performed multiple times to determine change due to displacement. By repetitively scanning with ultrasound, the position of tissue at different times is determined.

Ultrasound data is obtained. At least some of the ultrasound data is responsive to the induced wave. A region of interest is monitored to detect the induced wave. This detection region is monitored by ultrasound. For example, B-mode scans are performed to detect tissue displacement caused by the induced wave. Doppler, color flow, or other ultrasound mode may be used to monitor for the shear wave.

The monitoring is performed for any number of scan lines. For example, a single beam or four receive beams are formed in response to each transmission. After transmitting the excitation to generate the wave, transmissions are performed repetitively along a single scan line and receptions along the same scan line or adjacent scan lines. In other embodiments, other numbers of receive beams are formed in response to each tracking transmission. Any number of repetitions may be used, such as about 120 times. Some of the ultrasound data, such as at the beginning or end of the repetitions, may not be responsive to the induced wave.

Displacement of tissue caused by the wave is detected from the data received by the scanning. The echoes are detected using B-mode or Doppler detection. The displacement is detected from the differences for each spatial location over time. The difference between the tracking information and the reference information indicates displacement. For example, the velocity, variance, shift in intensity pattern (e.g., speckle tracking), or other information is detected from the received data and the reference data as the displacement.

The displacement caused by the force or stress is measured. A single displacement is determined by a comparison between the reference information and data from one scan in tracking. The one scan is timed to occur at a likely time of passing of the induced wave. In other embodiments, a displacement profile of response in the patient is determined. For example, the displacements over time for a location are determined. The spatial deviation of the tissue from the reference is determined at different times. The displacement may be measured over time at one or more locations.

The displacement measurement may begin before the stress or impulse ends, such as using a different frequency or coding. Alternatively, the displacement measurement begins after the impulse ends. Since the shear, longitudinal or other wave causing the displacement in tissue spaced from the point or region of stress takes time to travel, the displacement from a relaxed or partially stressed state to a maximum displacement and then to a relaxed state may be measured. Alternatively, the displacement is measured only while the tissue is relaxing to form the maximum.

The measurement is of the amount or magnitude of the displacement. The tissue is moved in any direction. The measurement may be along the scan line or axial dimension. The magnitude of the motion vector is determined. Alternatively, the measurement is along a two or three-dimensional direction or a direction of greatest movement.

In one embodiment using B-mode data, the data from different scans is correlated. For example, a current set of data is correlated multiple times with a reference set of data. Different relative translations and/or rotations between the two data sets are performed. The location of a sub-set of data centered at a given location in the reference set is identified in the current set.

The reference is a first set of data or data from another scan. The same reference is used for the entire displacement detection or the reference data changes in an ongoing or moving window.

The correlation is one, two or three-dimensional. For example, correlation along a scan line away and toward the transducer is used. For a two dimensional scan, the translation is along two axes with or without rotation. For three dimensional scanning, the translation is along three axes with or without rotation about three or fewer axes. The level of similarity or correlation of the data at each of the different offset positions is calculated. The translation and/or rotation with a greatest correlation represents the motion vector or offset for the time associated with the current data being compared to the reference.

Any now known or later developed correlation may be used, such as cross-correlation, pattern matching, or minimum sum of absolute differences. Tissue structure and/or speckle are correlated. Using Doppler detection, a clutter filter passes information associated with moving tissue. The velocity of the tissue is derived from multiple echoes. The velocity is used to determine the displacement towards or away from the transducer. Alternatively, the relative or difference between velocities at different locations may indicate strain or displacement.

As the wave propagates along the scan line, the B-mode intensity may vary due to displacement of the tissue. Data from a plurality of spatial locations (e.g., along the scan line) is correlated as a function of time. Any elasticity or shear detection may be used. For each depth or spatial location, a correlation over a plurality of depths or spatial locations (e.g., kernel of 64 depths with the center depth being the point for which the profile is calculated) is performed. Two or three-dimensional displacement in space may be used. One-dimensional displacement along a direction different from the scan line or beam may be used.

The spatial offset with the highest or sufficient correlation at a given time indicates the amount of displacement. Displacements may be determined for a given location at different times. The temporal profile for a given location indicates detection of the wave. The different profiles correspond to different repetitions of acts 34 and 36.

Using the profile, a given displacement may be selected as the displacement to be used for calculating attenuation. Any criteria may be used, such as the maximum displacement. The profile is examined for a non-noise or single instance of variation. A peak in the profile, with or without temporal low pass filtering, indicates the passing of the wave front. The greatest displacement is selected, but the average or other displacement statistic may be used. In other embodiments, the displacement, whether maximum or not, at a given time (e.g., 10 milliseconds after generation or X milliseconds per unit of distance from the focal region) is used.

The displacement profile may be smoothed or filtered for the maximum calculation. In other embodiments, the raw or unfiltered displacement curve may be used. The maximum value over the entire or portion of the profile is identified or determined. Other techniques may be used to detect the peak in the profile.

Figure 3:
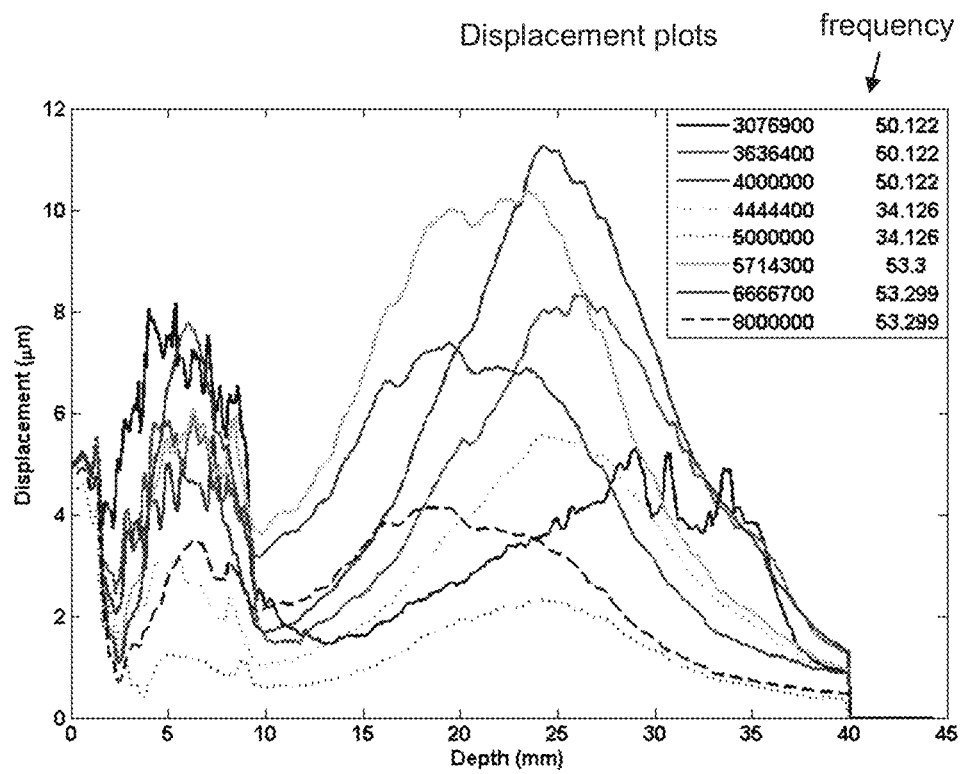
FIG. 3 is a graph illustrating example displacements of the tissue as a function of depth.

The transmission of acoustic beams for applying stress (i.e., inducing displacement in tissue) is repeated. The repetitions are with different center frequencies. Other characteristics are the same or may be different. Any number of repetitions and corresponding different center frequencies may be used. For example, FIG. 3 shows use of eight different center frequencies for the pushing pulses and the resulting maximum displacements as a function of depth. Since the frequency may result in change in amplitude to keep within limitations on transmit, the voltage associated with the generated beam may vary. The value next to the frequency represents a measure of voltage. The voltage is the same in other embodiments. Similarly, the tracking of act 36 associated with each transmission of act 34 is repeated.

The repetitions occur for a given location along the scan line. Displacement for other locations may be determined, such as to calculate attenuation for different depths. Using the same pushing transmissions and tracking scanning, displacements in response to different center frequencies of the pushing pulse are determined for different locations along a scan line. Any number of locations may be sampled, such as tens or hundreds of locations. Displacement estimates are accumulated for each depth in the acoustic path of acoustic radiation force impulse from all available pairs of displacement and frequency.

Additional transmissions and receptions may not be needed for determining displacements of locations along a same scan line. Alternatively, the scan line is divided into different depth ranges and acts 34 and 36 are performed separately for the different ranges.

Displacements along other scan lines may be determined. For scan lines near or adjacent to the scan line of the pushing beam, the same pushing pulse may be used. The tracking is along the different scan lines. Alternatively or additionally, the transmission of the pushing pulses at different frequencies and corresponding scanning for tracking are repeated for different scan lines. In one embodiment, the method is performed for each of B-mode or other scan sample locations in an entire field of view or a region of interest. Less or more dense sampling may be used for measuring displacement than for B-mode or other imaging. The displacements are measured for a single location or over a one, two, or three-dimensional distribution.

The locations for measuring displacement may be limited. For example, shear waves may not propagate in fluid tissue. Displacement of longitudinal waves in fluid or fluid tissue may be unreliable. Other tissue, fluid, or bone may result in accurate displacement measures. Tissue may be classified or segmented to identify specific locations for which the attenuation is to be calculated. Any classification may be used. For example, a signal-to-noise ratio of displacement is measured. If the signal-to-noise ratio is below a threshold, then the displacements from the corresponding location are not used. As another example, a signal-to-noise ratio or signal shape associated with speckle is used to classify tissue as soft tissue. Displacement is measured for soft tissue locations and not other locations.

In the example embodiment of acts 30, 32, 34, and 36, reference information is obtained, then a pushing pulse at one frequency is transmitted, then the displacement is tracked, then a pushing pulse at another frequency is transmitted, and then the displacement is tracked. This sequence is performed along a given scan line. The sequence is repeated for other scan lines. Other sequences and/or interleaving may be used. For example, pushing pulses at the same frequency for different scan lines are transmitted and resulting displacement tracked before pushing pulses at another frequency are used. As another example, reference information for all scan lines is acquired before sequencing through for causing and measuring displacement at different frequencies on different scan lines.

The tissue may be moving, such as due to cardiac motion and/or breathing of the patient. The transducer and/or patient may move, introducing relative motion. The transmissions and tracking of act 28 may account for the motion. For example, B-mode information is acquired interleaved with the detection of act 28. The B-mode information is from static tissue, such as spaced away from the heart. The B-mode information may be correlated or otherwise tracked to determine any transducer to patient relative motion. The difference in position due to the motion may be subtracted from or otherwise accounted for in the measured displacement. As another example, a region is tracked over time. The scan line used for the detection of act 28 is repositioned to be directed at the same tissue, such as to counteract cardiac or breathing motion. Other techniques for accounting for sources of motion (e.g., other motion compensation approaches) may be used, such as cardiac gating and breath holding.

In act 38, acoustic attenuation or absorption is calculated. The attenuation or absorption is calculated from the displacements. The displacements responsive to pushing pulses at different frequencies are used to determine attenuation or absorption of the tissue. The displacement responses to differences in frequency may be used to account for other unknowns, such as tissue stiffness.

The displacements used for the calculation are from one location. In another embodiment, the displacements for different frequencies and for different locations are used. The displacements along the same scan line and/or along multiple scan lines may be used.

Any function may be used. In one embodiment, the attenuation or absorption is calculated as a function of the difference in frequencies of the push pulses, the displacements caused by the different frequency pushing pulses, and derivatives of the displacements. For example, the displacement, $s_d$, is a function of the frequency, f, used for the pushing pulse and the depth, z, along the scan line. The logarithm of the displacement may be used to place the absorption into a linear domain. The displacement may be represented as:

$$\ln(s_d(z, f)) = R(f, z) - \alpha_{total}(f, z)$$
$$= -f \int_0^z \alpha(z) dz + R(f, z)$$

where R is a residual, such as to account for variance associated with any other factors, and $\alpha$ is the absorption coefficient. The residual, R, may be considered constant within the range of frequencies used for the pushing pulses. Solving for the attenuation provides:

$$\alpha(z) = \frac{1}{t_+ - t_-} \int_{t_-}^{t_+} \frac{\partial^2}{\partial z \partial f} [\ln(s_d(f, z))] dt$$

The absorption coefficient only affects the magnitude of the displacement inside tissue, such that:

$$s_d(z, f) \propto \alpha(z) \cdot f \cdot I(z, f)$$
$$\propto \alpha(z) \cdot f \cdot \gamma(f) \cdot I_{water}(z) \cdot e^{-f \int_{z0}^z (\alpha(z)) dz}$$

where I is the intensity in water conditions and $\gamma$ is the probe frequency dependent efficiency. Given two frequencies, $f_i$ and $f_j$, for the pushing pulses, the ratio is taken on both sides of the equation. Followed by logarithm and derivative operations, the absorption is represented as:

$$\alpha(z) = \frac{1}{f_j - f_i} \cdot \frac{s_d(z, f_j)}{s_d(z, f_i)} \cdot \left( \frac{s_d'(z, f_i)}{s_d(z, f_j)} - \frac{s_d(z, f_i) \cdot s_d'(z, f_j)}{s_d^2(z, f_j)} \right)$$

where $s_d'$ is the derivative of displacement over range. The absorption coefficient has the unit of 1/MHz*1/cm. Using the difference in frequencies, displacements at different frequencies and depths, and derivatives of the different displacements, the absorption coefficient is calculated.

Figure 4:
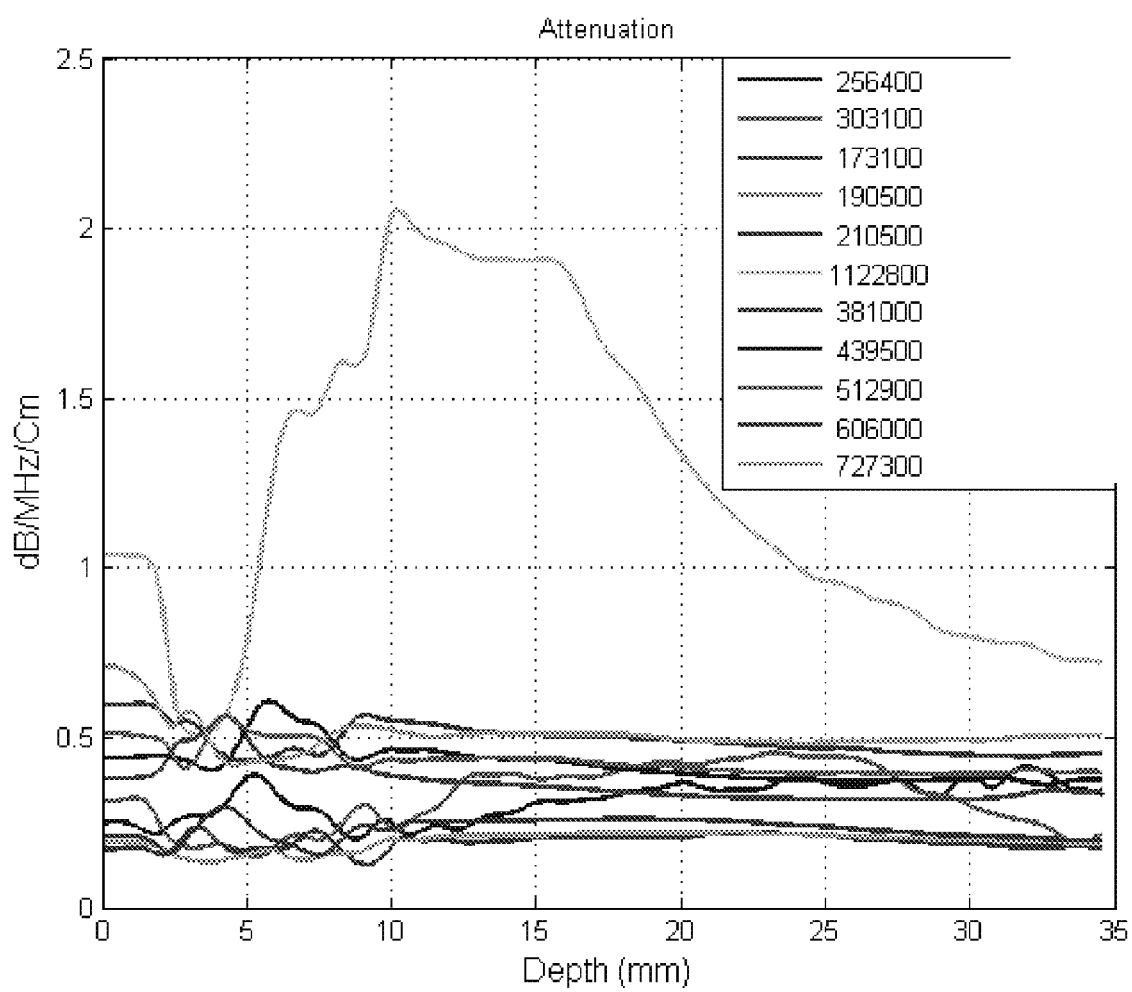
FIG. 4 is a graph illustrating example attenuation as a function of depth using the displacements of FIG. 4.

The calculation may be repeated for different frequency combinations and corresponding displacements. For example, FIG. 4 shows attenuation determined for different pairs of frequencies. Each line shows attenuation as a function of depth along a same scan line based on maximum displacements for two different frequencies. The results may be averaged, selected, or otherwise combined to determine attenuation for each depth. In the example of FIG. 4, one outlier attenuation is shown. The outlier may be removed by filtering or discarded prior to combination. Alternatively, the outlier is included in the combination.

Other functions may be used. In one embodiment, a regression is used. In other embodiments, a back-projection type of iterative algorithm may be used to estimate the absorption at each location. The displacements and corresponding frequencies for different locations are solved to determine attenuation or absorption along the scan line. The maximum displacements or the displacement profiles (e.g., displacement over time) may be used in the solution.

The attenuation and/or absorption may be specifically calculated as such. Alternatively, the attenuation is calculated and used as a calculated absorption or vice versa. For example, the calculated absorption may be used as the measure of attenuation. In other embodiments, a function relates the absorption to the attenuation. The function may be fixed, such as an average ratio, or may adapt by the type of tissue or ultrasound detected characteristic.

The attenuation or absorption is determined for one location. The attenuation or absorption may be determined for multiple depths along a same scan line. The calculations for different depths may be independent of calculations for other depths. Alternatively, the information from different depths is used to calculate for any given depth. In other embodiments, the acoustic absorption or attenuation is calculated for each of a plurality of locations distributed in two or three dimensions. The calculations are performed by location or by scan line along a plurality of different scan lines.

In act 40, the acoustic absorption or attenuation is displayed. The display is text. For example, a value representing attenuation at a location or an average attenuation for a region of interest is displayed. Alternatively, a graph may be displayed. For example, the attenuation as a function of depth is displayed. The attenuation for different lines may be displayed on a same graph or on different graphs.

In one embodiment, the display is an image representing a two-dimensional, spatial distribution of attenuation or absorption. An image or sequence of images may be generated to display the attenuation or absorption.

The attenuation or absorption is used for a color overlay or other modulation of display values. Color, brightness, luminance, hue, or other characteristic is modulated as a function of the attenuation or absorption. The attenuation or absorption values are in a display format or may be scan converted into a display format. The values are color or gray scale data, but may be data prior to mapping with gray scale or color scale. The values may be mapped linearly or non-linearly to the display values.

The image represents the attenuation or absorption information for the different locations. Where the values are determined for all of the grid points in a region of interest or field of view, the pixels of the display represent the attenuation or absorption for that region. The display grid may be different from the scan grid and/or grid for which values are calculated. Scan conversion, nearest neighbor selection, interpolation and/or extrapolation may be used to conform the attenuation or absorption resolution to the display resolution.

The image may include other data. For example, B-mode or other data representing tissue, fluid, or contrast agents in the same region or other regions is included. The attenuation or absorption data is used for an overlay of or combination with the other data.

In other embodiments, a three-dimensional distribution of the attenuation or absorption is calculated. The values may be rendered to a two-dimensional representation of the volume, such as through surface or projection rendering.

In act 42, settings for subsequent transmissions, receptions, or imaging adapt to the attenuation or absorption. For example, high intensity focused ultrasound (HIFU) treatment adapts as a function of the acoustic attenuation or absorption. Greater absorption by tissue may allow for lower amplitude, shorter duration, smaller aperture, or other decrease in power delivered for treatment. Lesser absorption may alter treatment planning to include application of more acoustic power to provide the desired dose.

Various aspects of the transmission, scanning, and/or detecting may be controlled. Values for different parameters are set. In one embodiment, the values are set based on a selected configuration. For example, the user selects shear wave or ARFI imaging. In response, predetermined parameters are loaded for operating the system. The predetermined parameters are the same for every application of that type or mode of imaging. Alternatively, further selections, such as imaging the liver or other type of tissue, for a given mode may result in configuring with different values. Further alteration is provided in response to estimated attenuation or absorption. For example, a lower transmit and/or receive frequency may be used for tissue associated with greater attenuation.

Example types of parameters for which the values may be set are a transmit frequency, line spacing, F-number, pulse repetition frequency, line sampling count, acoustic energy amplitude, pulse length, receive frequency, or combinations thereof. Different, additional, or fewer parameters may be set with different values.

The adaptation occurs during B-mode, Doppler, color flow, contrast agent, tissue Doppler motion, ARFI, shear wave, or other imaging and/or during therapy. Adaptive optimization may be applied prior to acquiring a static image or continuously during real-time imaging. For example, the attenuation or absorption is determined prior to presenting an image for diagnosis to the user. Subsequent images use settings adapted based on the attenuation or absorption, at least during a given examination of a patient for a sonography session. As another example, the adaptation continues or is performed at different times during the examination. Periodic or triggered adaptation may be used.

The attenuation, absorption, or data derived therefrom is used to set the parameter value. A look-up table or calculation (e.g., applying the feedback as a variable in a function) is used to determine the parameter value. For example, an average absorption above a threshold results in a value of X while the average absorption between the threshold and another threshold results in a value of Y. Any resolution (e.g., from binary to three or more ranges) of parameter value setting may be used.

Figure 5:
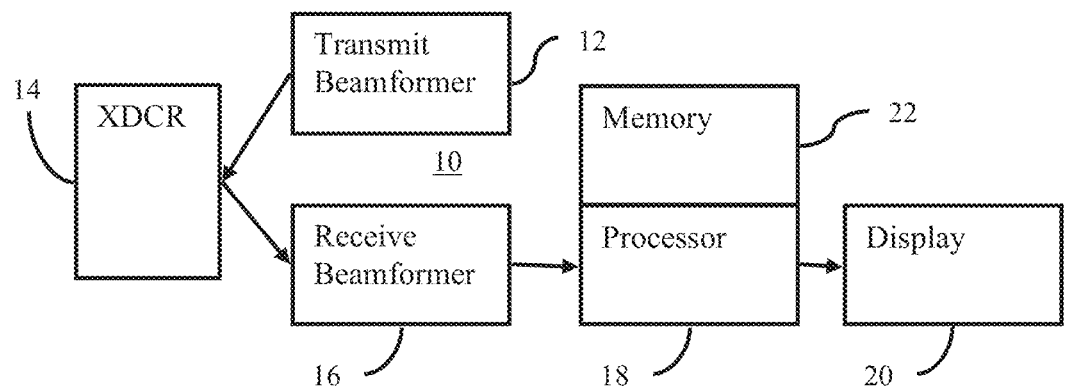
FIG. 5 is a block diagram of one embodiment of a system for measuring acoustic absorption or attenuation of ultrasound.

FIG. 5 shows one embodiment of a system 10 for measuring acoustic absorption of ultrasound. The system 10 implements the method of FIG. 2 or other methods. The system 10 includes a transmit beamformer 12, a transducer 14, a receive beamformer 16, an image processor 18, a display 20, and a memory 22. Additional, different or fewer components may be provided. For example, a user input is provided for user interaction with the system.

The system 10 is a medical diagnostic ultrasound imaging system. In alternative embodiments, the system 10 is a personal computer, workstation, PACS station, or other arrangement at a same location or distributed over a network for real-time or post acquisition imaging.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. The waveforms are generated with a programmable center frequency and duration. Waveforms with different center frequencies may be generated at different times.

Upon transmission of acoustic waves from the transducer 14 in response to the generated waveforms, one or more beams are formed. For measuring attenuation or absorption, beams along one or more scan lines are generated. A sequence of transmit beams may be generated to scan a two or three-dimensional region. Sector, Vector®, linear, or other scan formats may be used. The same region or line may be scanned multiple times. A sequence of scans along the same line or lines is used. In alternative embodiments, the transmit beamformer 12 generates a plane wave or diverging wave for more rapid scanning.

The same transmit beamformer 12 generates impulse excitations or electrical waveforms for generating acoustic energy to cause displacement and generates other imaging waveforms. In alternative embodiments, a different transmit beamformer is provided for generating the impulse excitation. The transmit beamformer 12 causes the transducer 14 to generate high intensity focused ultrasound waveforms, such as waveforms for acoustic radiation force or other pushing pulses of different frequencies at different times.

The transducer 14 is an array for generating acoustic energy from electrical waveforms. For an array, relative delays and/or phasing focus the acoustic energy. A given transmit event corresponds to transmission of acoustic energy by different elements at a substantially same time given the delays. The transmit event provides a pulse of ultrasound energy for displacing the tissue. The pulse is an impulse excitation. Impulse excitation includes waveforms with many cycles (e.g., 500 cycles) but that occurs in a relatively short time to cause tissue displacement over a longer time.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer 14. The elements connect with channels of the transmit and receive beamformers 12, 16. Alternatively, a single element with a mechanical focus is used.

The receive beamformer 16 includes a plurality of channels with amplifiers, delays, and/or phase rotators, and one or more summers. Each channel connects with one or more transducer elements. The receive beamformer 16 is configured by hardware or software to apply relative delays, phases, and/or apodization to form one or more receive beams in response to each imaging transmission. Receive operation may not occur for echoes from the impulse excitation used to displace tissue. The receive beamformer 16 outputs data representing spatial locations using the receive signals. Relative delays and/or phasing and summation of signals from different elements provide beamformation. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or other band. The receive beamformer 16 may isolate information at the fundamental or transmit frequencies.

In coordination with the transmit beamformer 12, the receive beamformer 16 generates data representing the region at different times. After the acoustic impulse excitation, the receive beamformer 16 generates beams representing one or more locations at different times. By scanning the region of interest with ultrasound, data (e.g., beamformed samples) is generated.

The receive beamformer 16 outputs beam summed data representing spatial locations. Data for a single location, locations along a line, locations for an area, or locations for a volume are output. Dynamic focusing may be provided. The data may be for different purposes. For example, different scans are performed for B-mode or tissue data than for displacement. Alternatively, the B-mode data is also used to determine displacement. As another example, data for displacement-based attenuation measurement is performed with a series of shared scans and B-mode or Doppler scanning is performed separately or using some of the same data.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof or other now known or later developed device for detecting, determining displacement, and calculating attenuation or absorption. In one embodiment, the processor 18 includes one or more detectors and a separate processor. The separate processor is a control processor, general processor, digital signal processor, application specific integrated circuit, field programmable gate array, network, server, group of processors, data path, combinations thereof or other now known or later developed device for determining displacement and calculating attenuation and/or absorption. For example, the separate processor is configured by hardware and/or software to perform and/or cause any combination of one or more of the acts shown in FIG. 2.

In one embodiment, the processor 18 is configured to determine spatial offsets of tissue in response to the acoustic radiation force of different frequencies at the different times. The displacement or offset of tissue caused by a stress is measured. Using correlation or other technique, the amount of displacement at one or more times is determined. The stress is applied at different times with different frequencies. The offsets resulting from the different frequencies is measured. The offsets for different frequencies may be measured for one or more locations, such as for a plurality of locations along a scan line.

The processor 18 is configured to determine an acoustic absorption or attenuation of the tissue as a function of the spatial offsets. The offsets measured for the different frequencies are used to solve for attenuation or absorption. Offsets measured for different locations may be used. The acoustic absorption or attenuation is calculated as a function of the spatial offsets for the different frequencies and different locations.

The processor 18 is configured to generate a display using the absorption or attenuation. Text, graph, or image display is generated. Alternatively or additionally, the processor 18 controls operation of therapy or imaging based on the attenuation or absorption.

The processor 18 operates pursuant to instructions stored in the memory 22 or another memory for measuring acoustic attenuation of ultrasound. The processor 18 is programmed for detecting displacement, calculating attenuation or absorption, and/or using attenuation or absorption.

The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a CRT, LCD, projector, plasma, or other display for displaying text, graphs, two-dimensional images or three-dimensional representations. The display 20 is configured by the processor 18 or other device by input of the signals to be displayed as an image. The display 20 displays an image representing attenuation or absorption for different locations in a region of interest or an entire image. The display 20 may alternatively or additionally display text or graph representing attenuation or absorption at a location or region of interest.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:
1. A method for measuring acoustic absorption of ultrasound, the method comprising:
transmitting, with a transducer, a first acoustic beam;
receiving reference information representing tissue in a reference position in response to the transmission of the first acoustic beam;
transmitting, with the transducer, a second acoustic beam at a second center frequency;
tracking second displacement from the reference position caused by the transmission of the second acoustic beam;

transmitting, with the transducer, a third acoustic beam at a third center frequency, the third center frequency different than the second center frequency;

tracking third displacement from the reference position caused by the transmission of the third acoustic beam;

calculating acoustic absorption of the tissue as a function of the second and third displacements and a difference between the second and third center frequencies as a variable; and displaying the acoustic absorption.

2. The method of claim 1 wherein receiving the reference information comprises acquiring B-mode data representing the tissue.

3. The method of claim 1 wherein transmitting the second and third acoustic beams each comprises transmitting acoustic radiation force having a greater power than the first beam.

4. The method of claim 1 wherein transmitting the second and third acoustic beams each comprises transmitting with a duration being at least 50 micro seconds.

5. The method of claim 1 wherein tracking the second and third displacements each comprises transmitting, repetitively, at a tracking center frequency different than the second and third center frequencies, and receiving tracking information, repetitively, in response to the transmitting at the tracking center frequency, and calculating displacement as a function of time from the tracking information, the second and third displacements each comprising a maximum of the displacement as a function of time in response to the second and third acoustic beams, respectively.

6. The method of claim 1 wherein tracking the second and third displacements comprise identifying the second and third displacements as maximum axial displacements in response to the second and third acoustic beams, respectively.

7. The method of claim 1 wherein calculating the acoustic absorption comprises calculating an attenuation.

8. The method of claim 1 wherein calculating the acoustic absorption comprises calculating as a function of the difference between the second and third frequencies, the second and third displacements, and derivatives of the second and third displacements.

9. The method of claim 1 further comprising repeating the tracking of the second and third displacements for other ranges along a scan line, and wherein calculating comprises calculating as a function of the second and third displacements for the other ranges.

10. The method of claim 1 further comprising:
transmitting, with the transducer, a fourth acoustic beam at a fourth center frequency, the fourth center frequency different than the second and third center frequencies; and tracking fourth displacement from the reference position caused by the transmission of the fourth acoustic beam;

wherein calculating comprises calculating as a function of the fourth displacement.

11. The method of claim 1 wherein displaying comprise displaying a text or graph representing the acoustic absorption.

12. The method of claim 1 wherein the transmitting, receiving, and tracking acts are performed for a plurality of depths on a plurality of scan lines, wherein calculating comprises calculating the acoustic absorption for each of the depths on the plurality of scan lines, and wherein displaying comprises displaying an image representing at least two-dimensional distribution of the acoustic absorption.

13. The method of claim 1 further comprising:
adapting a transmit frequency, line spacing, F-number, pulse repetition frequency, line sampling count, acoustic energy amplitude, acoustic energy pulse length, or combinations thereof as a function of the acoustic absorption.

14. In a non-transitory computer readable storage medium having stored therein data representing instructions executable by a programmed processor for measuring acoustic attenuation of ultrasound, the storage medium comprising instructions for:
detecting displacements of tissue with ultrasound from an ultrasound system, the displacements being in response to stresses at different frequencies caused by the ultrasound system; and calculating acoustic attenuation as a function of the displacements responsive to the stresses at the different frequencies and a variable that is a difference between the different frequencies.

15. The non-transitory computer readable storage medium of claim 14 wherein detecting comprises detecting a first of the displacements of the tissue in response to acoustic radiation force at a first frequency of the different frequencies and detecting a second of the displacements of the tissue in response to acoustic radiation force at a second frequency of the different frequencies, the second frequency different than the first frequency, and wherein calculating comprises calculating the acoustic attenuation as a function of the first and second displacements.

16. The non-transitory computer readable storage medium of claim 14 wherein detecting the displacements comprises detecting maximum displacements of the tissue.

17. The non-transitory computer readable storage medium of claim 14 wherein calculating comprises calculating the attenuation as a function of the displacements and as a function of the different frequencies.

18. The non-transitory computer readable storage medium of claim 14 further comprising:
controlling high intensity focused ultrasound treatment as a function of the acoustic attenuation.

19. The non-transitory computer readable storage medium of claim 14 wherein calculating the acoustic attenuation comprises calculating as a function of the difference between the different frequencies, the displacements, and derivatives of the displacements.

* * * * *